United States Patent
Finley

(10) Patent No.: US 11,517,447 B2
(45) Date of Patent: Dec. 6, 2022

(54) DISPOSABLE HANDLE FOR MEDICAL INSTRUMENTS

(71) Applicant: NEXTREMITY SOLUTIONS, INC., Warsaw, IN (US)

(72) Inventor: Adam Finley, Warsaw, IN (US)

(73) Assignee: MEDARTIS AG, Basel (CH)

( * ) Notice: Subject to any disclaimer, the term of this patent is extended or adjusted under 35 U.S.C. 154(b) by 0 days.

(21) Appl. No.: 16/961,866

(22) PCT Filed: Feb. 27, 2019

(86) PCT No.: PCT/US2019/019842
§ 371 (c)(1),
(2) Date: Jul. 13, 2020

(87) PCT Pub. No.: WO2019/168987
PCT Pub. Date: Sep. 6, 2019

(65) Prior Publication Data
US 2021/0007862 A1    Jan. 14, 2021

Related U.S. Application Data

(60) Provisional application No. 62/636,114, filed on Feb. 27, 2018.

(51) Int. Cl.
*A61F 2/46* (2006.01)
*A61B 17/00* (2006.01)

(52) U.S. Cl.
CPC ............ *A61F 2/4603* (2013.01); *A61B 17/00* (2013.01); *A61B 2017/00367* (2013.01);
(Continued)

(58) Field of Classification Search
CPC ......... A61F 2/4603; A61B 2017/00367; A61B 2017/0042; A61B 2017/00424; A61B 2017/0046; A61B 2017/00464
See application file for complete search history.

(56) References Cited

U.S. PATENT DOCUMENTS

| 4,421,108 A | 12/1983 | Cabrera et al. |
| 5,443,471 A | 8/1995 | Swajger |

(Continued)

OTHER PUBLICATIONS

International Search Report and Written Opinion of the International Searching Authority for International Application No. PCT/US2019/019842 dated May 10, 2019.
(Continued)

*Primary Examiner* — Kevin T Truong
*Assistant Examiner* — Diana Jones
(74) *Attorney, Agent, or Firm* — Heslin Rothenberg Farley & Mesiti P.C.; Victor A. Cardona, Esq.

(57) ABSTRACT

An apparatus for releasably holding a surgical tool having a body, the body having a longitudinal axis, a monolithic construction, and a shape apportioned to be grasped by a human hand, with body further having a tool engaging portion, a hand receiving portion, and a button pressing portion. A longitudinal bore is disposed along the longitudinal axis of the body, and on one end. A transverse bore is disposed through the body into the longitudinal bore, with the transverse bore disposed such that the longitudinal axis of the transverse bore intersects the longitudinal axis of the longitudinal bore. A button disposed on and pivotably attached at a resilient member to the button pressing portion of the exterior of the body, with the button being proximal to the tool engaging portion. The button has a button bore and a boss extending from the button bore into the transverse bore which is alignable with the longitudinal bore. The button is disposed on the body to be thumb pressable, the button suitable for selectively engaging a corresponding groove on surgical tool.

9 Claims, 3 Drawing Sheets

(52) U.S. Cl.
CPC .............. *A61B 2017/00424* (2013.01); *A61B 2017/00464* (2013.01); *A61B 2017/00862* (2013.01); *A61B 2017/00955* (2013.01)

(56) References Cited

U.S. PATENT DOCUMENTS

| | | |
|---|---|---|
| 5,499,986 A | 3/1996 | Dimarco |
| 5,582,615 A | 12/1996 | Foshee et al. |
| 7,381,207 B2 | 6/2008 | Duong et al. |
| 8,834,479 B2 | 9/2014 | Aux Epaules et al. |
| 2003/0191414 A1* | 10/2003 | Reiley ................ A61B 17/8819 606/167 |
| 2004/0064141 A1 | 4/2004 | Lechot |
| 2004/0133208 A1 | 7/2004 | Weikel et al. |
| 2011/0306952 A1 | 12/2011 | Chen et al. |
| 2015/0290040 A1* | 10/2015 | Vaughan ................ A61F 11/202 606/109 |
| 2017/0224399 A1 | 8/2017 | Coillard-Lavirotte et al. |
| 2018/0028339 A1* | 2/2018 | Loper ................ A61M 25/0097 |
| 2018/0214281 A1* | 8/2018 | Dykema ................ A61F 2/389 |

OTHER PUBLICATIONS

UK Examination Report dated Sep. 6, 2021.

\* cited by examiner

DISPOSABLE HANDLE FOR MEDICAL INSTRUMENTS

CROSS REFERENCE

This Application is a U.S. national phase entry under Section 371 of International Application No. PCT/US2019/019842 filed Feb. 27, 2019 and published in English as WO 2019/168987 A1, which claims the benefit of priority under 35 U.S.C. § 119(e) to U.S. Provisional Patent Application Ser. No. 62/636,114 filed Feb. 27, 2018. The contents of each of the prior applications are incorporated by reference herein.

TECHNICAL FIELD

The present invention relates to quick disconnect handles for a surgical instrument or device.

BACKGROUND OF THE INVENTION

It is often advantageous to the field to have an interface between the instrument handle and a surgical component that is quickly releasable, requires little manipulation to accomplish, and that can accommodate a variety of prosthetic component configurations for combination with a given inserter handle. Moreover, the known prior art, as shown below, does not disclose a single use device that incorporates these advantages.

U.S. Pat. No. 4,421,108 discloses a quick-release ratcheting holder for a surgical retractor which includes a spring detent to keep the holder from coming off the ring member when the retractor is relaxed.

U.S. Pat. No. 5,443,471 discloses a handle for use in implanting a prothesis has an elongate body portion and a post-retaining structure at the end of the body portion. The post-retaining portion or structure includes a core member which has a bore formed therein to receive a post connected, for example, to a broach or rasp. The core member also includes a channel formed therein in communication with the bore and a boss movable within the channel between a locked position at the distal end of the channel in communication with the bore and a released position. A spring and a collar are provided where the collar is adapted to slide over the core member, move the boss within the channel and retain the boss in the locked position while the spring is adapted to bias and/or move the collar toward the front end of the core to retain the boss. A movable sleeve fits over the collar and spring and is provided with a shoulder to engage and move the collar to release the boss within the channel.

U.S. Pat. No. 5,499,986 discloses a quick release handle apparatus for pulling an intramedullary nail includes a handle body with a sliding pushrod that moves an outer cylindrical member over an inner cylindrical member having locking elements. The locking elements engage an annular groove on a nail puller element that attaches to an intramedullary nail. The outer cylinder overlaps the inner cylinder at the locking balls to define the locking position.

U.S. Pat. No. 5,582,615 discloses an actuator handle for a surgical instrument that can be used in endoscopic surgery with the emphasis on applying hemostatic clips. The instrument receives a longitudinal input from the actuator handle and translates the input into relative component motion to apply the hemostatic clips. The improved handle is fabricated primarily from a reusable, engineering resin having exceptional resistance to degradation by steam sterilization. Other improvements to the actuator handle include a drive stem mechanism of unitary construction that can be removed from the actuator handle as an assembled unit to facilitate sterilization. The actuator handle is provided with a quick release mechanism to facilitate the removal and replacement of the drive stem mechanism. The improved actuator handle also features a ratchet mechanism that enables the user to incrementally adjust the longitudinal input force that is transmitted to the surgical instrument and includes a switch for selective operation of the same. The actuator handle also includes a safety lock mechanism integrated into the drive stem mechanism for selective engagement of the surgical instrument and the actuator handle to prevent accidental disconnection during a surgical procedure.

U.S. Pat. No. 7,381,207 discloses a quick disconnect assembly including a reusable assembly including a distal end having a male lip thereon; and, a disposable assembly having quick disconnect capabilities when utilized with the reusable assembly. The disposable assembly includes a stem section; a finger lock element; and, a detachable handle assembly. The finger lock element includes a distal finger lock element section having a threaded inner surface for engagement with a threaded outer surface of the stem section; and, a plurality of radially spaced fingers extending proximally from the distal finger lock element section. Each finger has a) a ramped surface for operatively engaging an associated ramp section on the stem section during use; and, b) a female lip at a proximal end thereof. The detachable handle assembly includes a proximal handle section having a distal end having an inner surface that is operatively engaged with an outer surface of the finger lock element so as to resist relative rotation and axial motion therebetween. A distal handle section of the detachable handle assembly includes a distal handle section having an inner surface that is operatively engaged with another outer surface of the stem section to resist relative rotation and axial motion therebetween. A breakaway collar of the detachable handle assembly is positioned between the proximal handle section and the distal handle section. When the disposable assembly is attached, the breakaway collar is an integral unit which prevents relative rotation between the proximal handle section and the distal handle section, the female lip engaging the male lip at a distal end of the reusable assembly, thereby securing the reusable assembly to the disposable assembly. The quick disconnect assembly may be used to provide only a mechanical connection or it may be provided with components for providing fluid transfer. In another embodiment, instead of only providing for single use, multiple use of a detachable assembly is provided by eliminating the breakaway collar and utilizing spring biasing means.

U.S. Pat. No. 8,834,479 discloses a prosthetic acetabular cup inserter and impactor has a body, and a cup engaging element disposed at a first end of the body and adapted to engage an inner surface of a cup with which it is used via outward biasing of the cup engaging element. The cup engaging element increases in cross-sectional area from an inner end thereof to a fullest transverse section, and decreases in cross-sectional area from said fullest transverse section to an outer end thereof. The cup engaging element has a tapered central bore engaged by a conically tapered actuation element moveable in the bore. The cup engaging element has a slot therethrough allowing the element to resiliently expand on movement of the actuator in the bore.

Thus, a need exists for quick release handles usable with a variety of surgical tools.

SUMMARY OF THE INVENTION

An apparatus for releasably holding a surgical tool has a body, the body having a longitudinal axis, a monolithic construction, and a shape apportioned to be grasped by a human hand, with the body further having a tool engaging portion, a hand receiving portion, and a button pressing portion. A longitudinal bore is disposed along the longitudinal axis of the body, and on one end. A transverse bore is disposed through the body into the longitudinal bore, with the transverse bore disposed such that the longitudinal axis of the transverse bore intersects the longitudinal axis of the longitudinal bore. A button disposed on and pivotably attached at a resilient member to the button pressing portion of the exterior of the body, with the button being proximal to the tool engaging portion. The button has a button bore and a boss extending from the button bore into the transverse bore which is alignable with the longitudinal bore. The button is disposed on the body to be thumb pressable, the button suitable for selectively engaging a corresponding groove on surgical tool such that the boss moves out of the groove when the button is pressed.

An apparatus for releasably holding a surgical tool has a body, the body having a longitudinal axis, a monolithic construction, and a shape apportioned to be grasped by a human hand, with body further having a tool engaging portion, a hand receiving portion, and a button pressing portion. A longitudinal bore is disposed along the longitudinal axis of the body, and on one end. A transverse bore is disposed through the body into the longitudinal bore, with the transverse bore disposed such that the longitudinal axis of the transverse bore intersects the longitudinal axis of the longitudinal bore. A button disposed on and pivotably attached at a resilient member to the button pressing portion of the exterior of the body, with the button being proximal to the tool engaging portion. The button has a button bore and a boss extending from the button bore into the transverse bore which is alignable with the longitudinal bore. The button is disposed on the body to be thumb pressable, the button suitable for selectively engaging a corresponding groove on surgical tool such that the boss is prevented from moving out of the groove when the button is pressed.

An apparatus for releasably holding a surgical tool has a body, the body having a longitudinal axis, a monolithic construction, and a shape apportioned to be grasped by a human hand, with body further having a tool engaging portion, a hand receiving portion, and a button pressing portion. A longitudinal bore is disposed along the longitudinal axis of the body, and on one end. A transverse bore is disposed through the body into the longitudinal bore, with the transverse bore disposed such that the longitudinal axis of the transverse bore intersects the longitudinal axis of the longitudinal bore. A button disposed on and pivotably attached at a resilient member to the button pressing portion of the exterior of the body, with the button being proximal to the tool engaging portion. The button has a first side, an opposing second side, a button bore and a boss extending from the button bore and alignable with the longitudinal bore. The first side is disposed on the body to be thumb pressable, and suitable for selectively engaging a corresponding groove on surgical tool such that the boss moves out of the groove when the button is pressed. The second side is disposed on the body to be index finger pressable, and suitable for selectively engaging a corresponding groove on surgical tool such that the boss is prevented from moving out of the groove when second side of the button is pressed.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

Corresponding reference characters indicate corresponding parts throughout the several views. The exemplary embodiments set forth herein are not to be construed as limiting the scope of the invention in any manner.

DETAILED DESCRIPTION OF THE INVENTION

Figure 1:
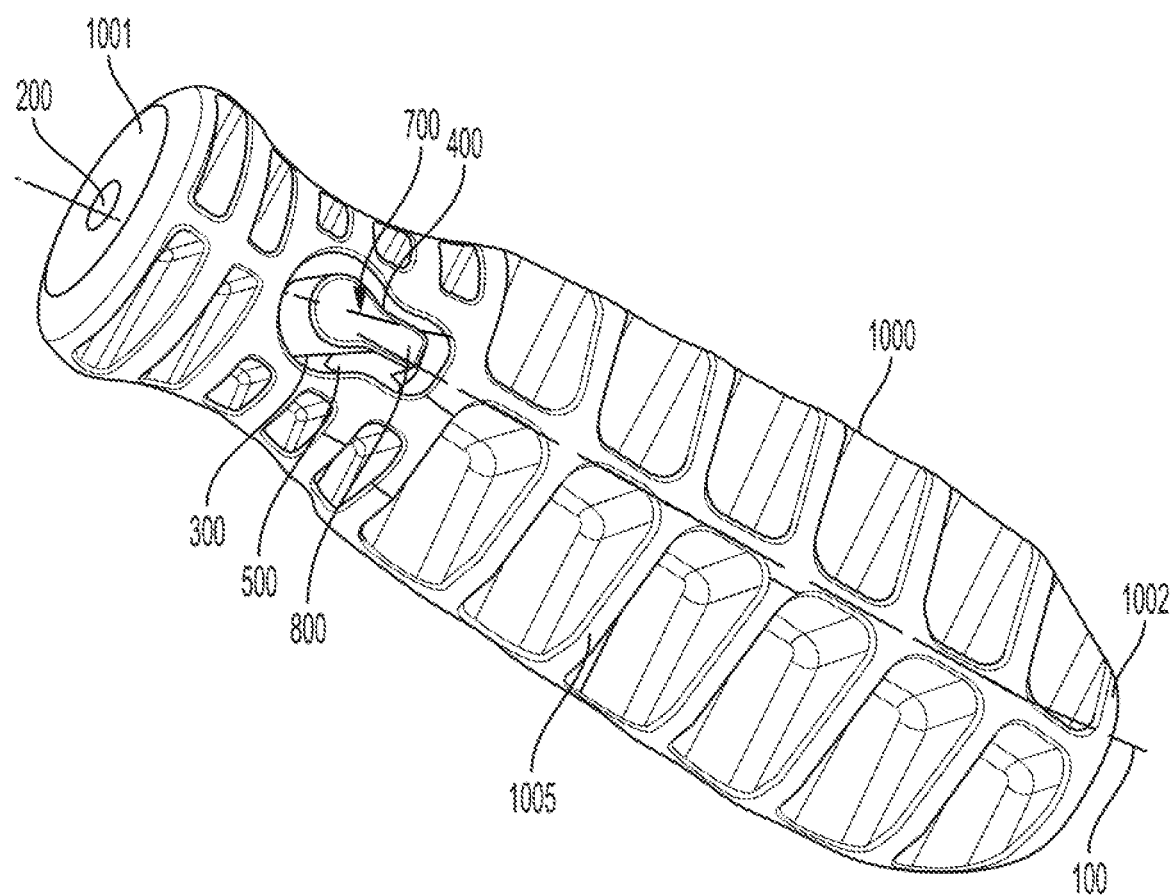
FIG. 1 shows a front perspective view of a disposable handle in accordance with the present invention.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. While this invention is satisfied by embodiments in many different forms, there is shown in the drawings, and will herein be described in detail, a preferred embodiment of the invention with the understanding that the present disclosure is to be considered as exemplary of the principles of the invention and is not intended to limit the invention to the embodiment illustrated. The scope of the invention will be pointed out in the appended claims.

Referring now to FIG. 1, there is shown a front perspective view of a disposable, releasable handle 1000 in accordance with the present invention. As illustrated in FIG. 1, handle 1000 may have a body 1005 preferably having a bulbous shape suitable for being held by a human hand. Handle 1000 further may have a proximal end 1001 and a distal end 1002. Body 1005 of handle 1000 may have a light weight, inexpensive, biologically inert material. Preferably, handle 1000 is comprised of polyacrylamide, polycarbonate, or acrylonitrile butadiene styrene ("ABS"). Handle 1000 is also of a uni-body or monolithic design as shown in FIG. 1. This uni-body construction makes handle 1000 easier to manufacture and stronger than a multicomponent design having the same materials of construction.

Referring again to FIG. 1, handle 1000 may have a longitudinal axis 100. Handle 1000 further may have longitudinal bore 200 disposed through handle 1000 along longitudinal axis 100. Longitudinal bore 200 is open at proximal end 1001 of handle 1000.

Referring again to FIG. 1, handle 1000 further may have a transverse bore 300. Transverse bore 300 is disposed through body 1005 of handle 1000 as illustrated in FIG. 1. Transverse bore 300 may have a longitudinal axis 700. Transverse bore 300 intersects with longitudinal bore 200. Preferably, transverse bore 300 is perpendicular to longitudinal bore 200. Transverse bore 300 may also have a first opening and a second opening.

Referring still to FIG. 1, handle 1000 further may have button 400. Button 400 is flexibly attached to handle 1000 as shown in FIG. 1. Button 400 may extend through transverse bore 300, intersecting longitudinal bore 200. Button 400 and transverse bore 300 may be disposed on body 1005 of handle 1000 such that button 400 is thumb accessible and/or depressible. Positioning button 400 closer to the proximal end 1001 of handle 1000, also positions button 400 closer to the tool engaging portion of handle 1000. Handle 1000 may be configured (e.g., shaped and dimensioned) to allow handle 1000 to be held, grasped, or used by a hand such that the fifth digit and hypothenar region are positioned in proximity to or around the distal end of handle 1002, with handle 1000 extending across the palm in the direction of the region between the first and second digits, such that the first digit or thumb may easily access and depress button 400.

Advantageously, because of the uni-body design, devices made in accordance with the present invention may not have additional components such as springs. Button 400 is connected to body 1005 by resilient member 800. Thus, the present invention may be less expensive to manufacture and simple to use. Moreover, because the device is inexpensive to make, it is an ideally suited single use (e.g. disposable) device. Cleanliness is assured because the device is removed from a sterile package and used only once.

Figure 2:
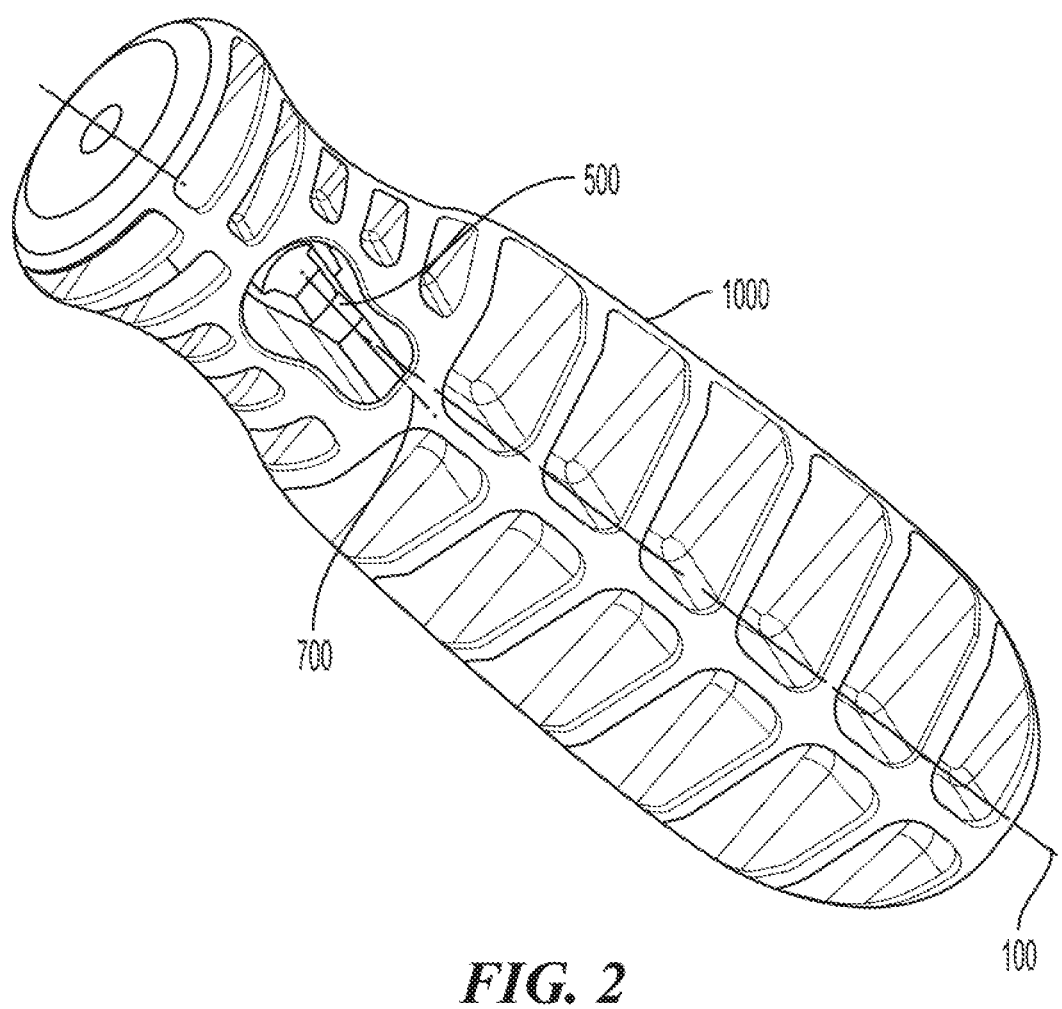
FIG. 2 shows an underside perspective view of the disposable handle of FIG. 1.

Referring now to FIG. 2, there is shown an underside perspective view of a disposable, releasable handle 1000 in accordance with the present invention. A backstop 500 is illustrated. Referring to FIGS. 1 and 2, button 400 has a thickness which may extend into transverse bore 300 in a longitudinal direction.

Figure 3:
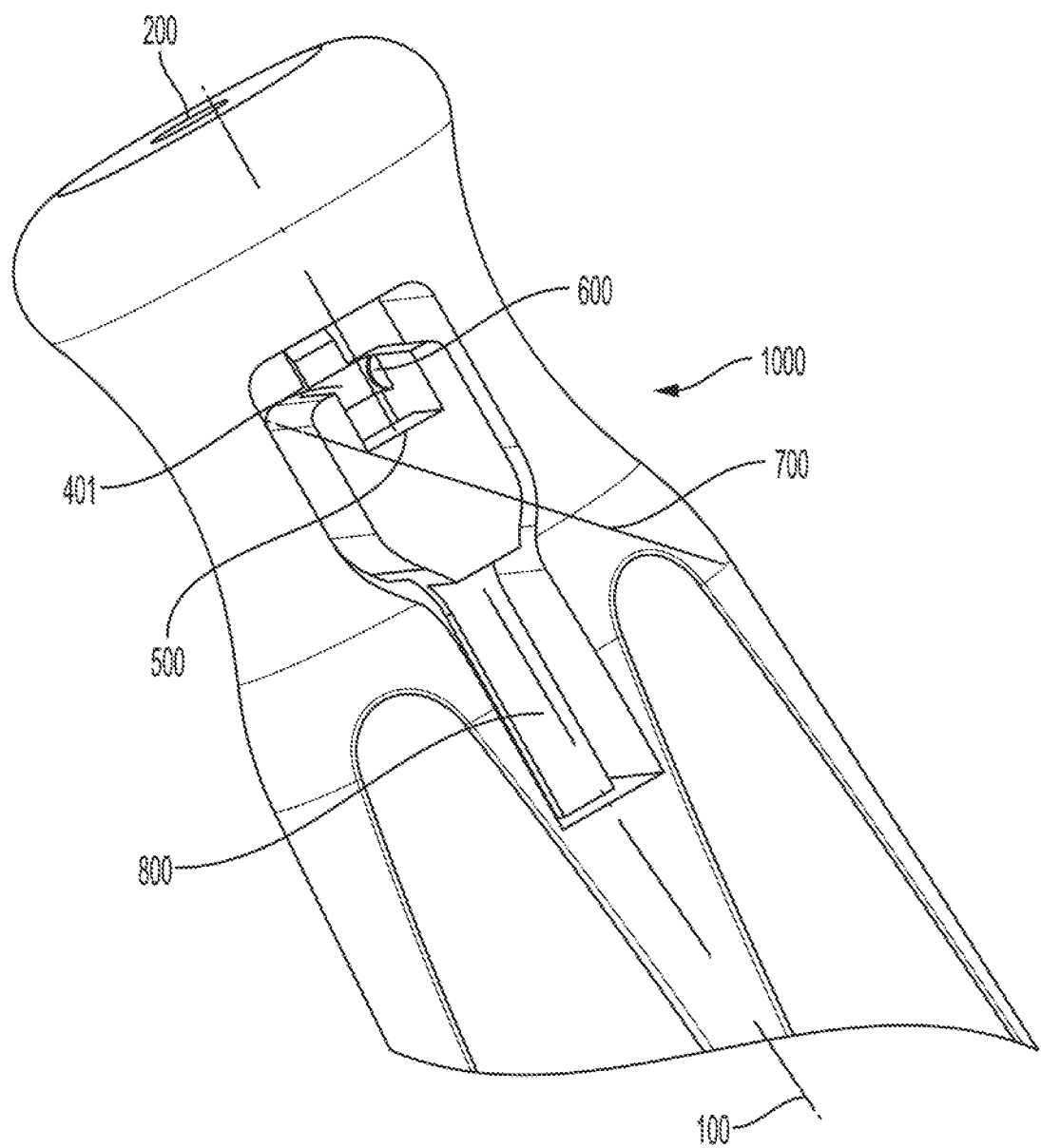
FIG. 3 shows an underside perspective view of the disposable handle of FIG. 1 with a boss in accordance with the present invention.

Referring now to FIG. 3, depicts an embodiment of handle 1000 with button having a button bore 401 and a boss 600. Button bore 401 may be a groove or a cutout portion of button 400, with button bore 401 configured to accommodate connection features (not shown) on the end of common surgical tool inserted into handle 1000, in longitudinal bore 200.

Referring now to FIGS. 1-3, it is contemplated that surgical instruments adapted to work with the mechanism of the present invention can be inserted into longitudinal bore 200 of handle 1000. The end of such a surgical instrument may be inserted into longitudinal bore 200 until the surgical instrument end contacts backstop 500, at which point further insertion may be inhibited. There may be embodiments of button 400 which may have a "click feature" which may engage with the inserted end of the tool. The click feature may engage with the tool, providing minimal resistance to disengagement forces, such as, for example, longitudinal forces caused by the effective end of the surgical tool becomes lodged and handle being pulled away. By depressing button 400, a transverse force may be applied to the end of the surgical tool, providing additional force to prevent the surgical instrument from being pulled out by disengagement forces. Under such embodiments, the tool may be removed by manually pulling the tool out of handle. In this embodiment, the button bore extends enough to engage the surgical tool, with the button underside having alignment features with a groove on the tool.

Further referring to FIGS. 1-3 surgical tools or instruments which are insertable into handle 1000, may have grooves or attachments to accommodate connectors on the handle 1000. Boss 600 is adapted to cooperate with a corresponding groove or indentation on a surgical tool (not shown) that may be inserted into longitudinal bore 200 of handle 1000. Once the surgical tool is inserted in to handle 1000, boss 600 is biased into the groove of the tool. However, a user may disengage the tool from handle 1000 by pressing button 400 such that boss 600 pivots out of the groove within the tool. The surgical tool may connect with boss 600 fitted into a tool groove providing significant resistance to disengagement forces. However, the tool may still be pulled in response to significant force being applied by a user to the surgical tool through handle 1000.

Referring to FIGS. 1-3, button 400 may have button bore 401 alignable with longitudinal bore 200, such that the surgical tool inserted into longitudinal bore 200 may extend into or through button bore 401. Boss 600 may be positioned within button bore to engage with the groove of the tool (not shown) inserted into longitudinal bore and extending into button bore 401. The term "button bore" is used but the button bore 401 may be a hole or a gap in button 400 and need not extend through button 400. Button bore 401 may also be dimensioned and shaped in any way so as to accommodate the tool for easier connection with boss 600.

In an alternative embodiment of the present invention, button 400 may extend through transverse bore 300, such that a first side of button 400 is within a first opening of transverse bore 300 and a second side of button 400 is within a second bore opening. Button 400 and transverse bore 300 may be disposed on body 1005 of handle 1000 such that button 400 is thumb accessible and/or depressible to a user. Positioning button 400 closer to the proximal end 1001 of handle 1000, also positions button 400 closer to the tool engaging portion of handle 1000. Handle 1000 may be configured (e.g. shaped and dimensioned) to allow handle 1000 to be held, grasped, or used by a hand such that the fifth digit and hypothenar region are positioned in proximity to or around the distal end of handle 1002, with handle 1000 extending across the palm in the direction of the region between the first and second digits, such that the first digit or thumb may easily access and depress the first side of button 400. Boss 600 may be biased away from longitudinal bore 200 (i.e. out of transverse bore 300). Button bore 401 may be sufficiently deep into button 400 to so that the surgical is inserted into button bore. By pressing the first side of button 400 boss 600 may engage a corresponding tool inserted into longitudinal bore 200. When button 400 is pressed, handle 1000 selectively engages or disengages a cooperating surgical instrument that has been inserted into longitudinal bore 200. The boss 600 engages the side of the tool directly opposed to button 400, so the surgical tool inserts into the button bore 401. In this embodiment, a user can control the strength of the connection between handle 1000 and any surgical tool or device inserted into longitudinal bore 200 of handle 1000. The second side of button 400 may be positioned such that the index finger may easily access and depress the second side of button 400. By pressing the second side of button 400, additional force may be applied to the surgical tool to prevent or inhibit the tool from being removed by disengagement forces. The tool may be disengaged from handle 1000 by pressing button 400 on the first side, such that boss 600 pivots out of the groove within the tool. In this embodiment, a user can control the strength of the bore connection between handle 1000 and any surgical tool or device inserted into longitudinal bore 200 of handle 1000.

The body (e.g. body 1005) may be made from a lightweight, disposable or recyclable material including, for example thermoplastic polymer and fiberglass reinforced polymer.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. An apparatus for releasably holding a surgical tool, said apparatus comprising:
   a body, said body comprising a longitudinal axis, a shape apportioned to be grasped by a human hand, a monolithic construction;
   a longitudinal bore, said longitudinal bore disposed along said longitudinal axis of said body, said longitudinal bore open on a proximal end of said body;
      wherein the longitudinal bore is positioned to receive the surgical tool at said proximal end of said body;
   a transverse bore, said transverse bore disposed through said body into said longitudinal bore, said transverse bore disposed such that a transverse longitudinal axis of said transverse bore intersects the longitudinal axis of said longitudinal bore and said transverse bore extends from a periphery of said body along said transverse longitudinal axis to said longitudinal bore;
   a button, said button disposed on and pivotably attached at a resilient member to the exterior of said body, said button being distal to said proximal end, said button further comprising a button bore bounded by an inner surface of said button and a boss extending from said inner surface into said button bore, said button bore received in said transverse bore and movable in the transverse bore such that said button bore is received in said longitudinal bore, said button disposed on said body to be thumb pressable, said button suitable for selectively engaging said boss with a corresponding groove on the surgical tool when the surgical tool is received in said longitudinal bore such that the boss moves out of said groove when said button is pressed.

2. The apparatus for releasably holding a surgical tool of claim 1, wherein said body comprises a lightweight, disposable, recyclable material selected from the group consisting of thermoplastic polymer and fiberglass reinforced polymer.

3. The apparatus for releasably holding a surgical tool of claim 1 wherein said boss extends radially into said button bore toward said longitudinal axis.

4. An apparatus for releasably holding a surgical tool, said apparatus comprising:
   a body, said body comprising a longitudinal axis, a shape apportioned to be grasped by a human hand, a monolithic construction;
   a longitudinal bore, said longitudinal bore disposed along said longitudinal axis of said body, said longitudinal bore open on a proximal end of said body;
      wherein the longitudinal bore is positioned to receive the surgical tool at said proximal end of said body;
   a transverse bore, said transverse bore disposed through said body into said longitudinal bore, said transverse bore disposed such that a transverse longitudinal axis of said transverse bore intersects the longitudinal axis of said longitudinal bore and said transverse bore extends from a periphery of said body along said transverse longitudinal axis to said longitudinal bore;
   a button, said button disposed on and pivotably attached at a resilient member to the exterior of said body, said button being distal to said proximal end, said button disposed on said body to be thumb pressable, said button further comprising a button bore bounded by an inner surface of said button and a boss extending from said inner surface into said button bore, said button bore received in said transverse bore and movable in the transverse bore, such that said boss is engageable with a corresponding groove on the surgical tool when the surgical tool is received in said longitudinal bore, and such that the boss is prevented from moving out of said groove when said button is pressed.

5. The apparatus for releasably holding a surgical tool of claim 4, wherein said body comprises a lightweight, disposable, recyclable material selected from the group consisting of thermoplastic polymer and fiberglass reinforced polymer.

6. The apparatus for releasably holding a surgical tool of claim 4 wherein said boss extends radially into said button bore toward said longitudinal axis.

7. An apparatus for releasably holding a surgical tool, said apparatus comprising:
   a body, said body comprising a longitudinal axis, a shape apportioned to be grasped by a human hand, a monolithic construction;
   a longitudinal bore, said longitudinal bore disposed along said longitudinal axis of said body, said longitudinal bore open on a proximal end of said body;
   wherein the longitudinal bore is positioned to receive the surgical tool at said proximal end of said body;
   a transverse bore, said transverse bore disposed through said body into said longitudinal bore, said transverse bore disposed such that transverse longitudinal axis of said transverse bore intersects the longitudinal axis of said longitudinal bore and said transverse bore extends from a periphery of said body along said transverse longitudinal axis to said longitudinal bore;
   a button, said button disposed on and pivotably attached at a resilient member to the exterior of said body, said button being distal to said proximal end, said button disposed through said body through said transverse bore, and said button having a first side and an opposing second side;
      said button comprising a button bore bounded by an inner surface of said button and a boss extending from said inner surface into said button bore and movable in the transverse bore such that said button bore is received in said longitudinal bore, said first side disposed on said body to be thumb pressable and such that the boss moves into said groove when said first side of the button is pressed; and said second side disposed on said body to be index finger pressable, and such that said boss is prevented from moving out of said groove when said second side of the button is pressed.

8. The apparatus for releasably holding a surgical tool of claim 7, wherein said body comprises a lightweight, disposable, recyclable material selected from the group consisting of thermoplastic polymer and fiberglass reinforced polymer.

9. The apparatus for releasably holding a surgical tool of claim 7 wherein said boss extends radially into said button bore toward said longitudinal axis.

\* \* \* \* \*